United States Patent
Sakurai

(10) Patent No.: US 6,857,317 B2
(45) Date of Patent: Feb. 22, 2005

(54) DEVICE FOR MEASURING A FOOD PHYSICALITY AND METHOD FOR MEASURING THE SAME

(75) Inventor: Naoki Sakurai, Higashihiroshima (JP)

(73) Assignee: Hiroshima University, Higashihiroshima (JP)

( * ) Notice: Subject to any disclaimer, the term of this patent is extended or adjusted under 35 U.S.C. 154(b) by 68 days.

(21) Appl. No.: 10/392,987

(22) Filed: Mar. 21, 2003

(65) Prior Publication Data

US 2003/0216875 A1 Nov. 20, 2003

(30) Foreign Application Priority Data

Mar. 28, 2002 (JP) ..................................... 2002-090988

(51) Int. Cl.⁷ ........................ G01N 29/12; G01N 33/02
(52) U.S. Cl. ........................... 73/579; 702/56; 426/231
(58) Field of Search .............................. 73/579, 432.1, 73/662; 702/56; 426/231

(56) References Cited

U.S. PATENT DOCUMENTS

| | | | | |
|---|---|---|---|---|
| 4,257,001 A | * | 3/1981 | Partain et al. .............. | 324/636 |
| 5,152,401 A | * | 10/1992 | Affeldt et al. .............. | 209/556 |
| 5,372,030 A | * | 12/1994 | Prussia et al. .................. | 73/37 |
| 5,691,473 A | * | 11/1997 | Peleg ........................... | 73/573 |
| 6,276,536 B1 | * | 8/2001 | Terasaki et al. ............. | 209/599 |
| 6,539,781 B1 | * | 4/2003 | Crezee ........................... | 73/81 |

FOREIGN PATENT DOCUMENTS

| | | | | |
|---|---|---|---|---|
| JP | A 11-190688 | | 7/1999 | |
| JP | 2000105226 A | * | 4/2000 | .......... G01N/29/12 |
| JP | A 2000-283975 | | 10/2000 | |

OTHER PUBLICATIONS

JPA 11–190688 Abstract & Translation—Jul. 13, 1999.

JPA 2000–283975 Abstract & Traslation Oct. 13, 2000.

* cited by examiner

*Primary Examiner*—Hezron Williams
*Assistant Examiner*—Rose M. Miller
(74) *Attorney, Agent, or Firm*—Oliff & Berridge, PLC

(57) ABSTRACT

A thrust jig with a concave-convex shape is pierced into a food sample to generate and detect an oscillation spectrum and an acoustic spectrum, which is analyzed in main component to calculate a main component value as the texture of the food sample.

16 Claims, 5 Drawing Sheets

DEVICE FOR MEASURING A FOOD PHYSICALITY AND METHOD FOR MEASURING THE SAME

BACKGROUND OF THE INVENTION

1. Field of the Invention

This invention relates to a device for measuring a physicality of a food such as an agricultural product and a method for measuring the food physicality. Particularly, this invention relates to a device and a method for measuring the texture of the food using an acoustic signal or an oscillating spectrum which is generated by piercing a probe with a given shape into the food.

2. Description of the Prior Art

A person judges his or her likes and dislikes for foods by various factors such as taste, flavor and color. Among the factors, the textures for foods are very important in the judgment of likes and dislikes. For example, the crispy texture of fresh lettuce and celery and the mature texture of pear affect on the likes and dislikes of the person. Such a texture of a food is originated from the kinetic property (elasticity or viscosity) of the food. Therefore, the food texture can be quantified by measuring the kinetic property such as elasticity or viscosity of the food.

Conventionally, various methods for measuring the kinetic property of the food have been proposed. For example, the method for quantifying the texture of noodles or pastas is disclosed in Japanese Patent Application Laid-open No. 11-190688. Until that time, the texture of the noodles or the pastas is dubiously defined. Moreover, the method for measuring textures of foods which particularly, babies like is disclosed in Japanese Patent Application Laid-open No. 2000-283975.

In a conventional technique as mentioned above, a plunger is pierced into a food and then, lifted to measure the texture of the food by utilizing the kinetic property (stress or adhesive force) which is loaded to the plunger. In order to perform a precise measurement, the shape of the plunger is improved and changed on the sort of food. With the conventional technique, however, it is difficult to measure textures of various foods precisely.

For example, it is difficult to define the mature degree of pear, the texture of which is drastically changed in ripe to turn into a so-called buttery state. Therefore, the texture of pear is defined in sense by a person of experience and thus, can not be quantified, which poses great problems on distributive trade.

FIG. 5 is a graph showing the flesh hardness of a pear with time which is measured by utilizing a rheometer (CONPAC-100 made by San Science Industries, Co. Ltd.). In the measurement, a conical shaped plunger is employed, and pierced into the pear processed in a given size at a given constant rate. The flesh hardness is estimated from the stress when the plunger is pierced by a predetermined distance.

FIG. 6 is a graph showing the mature degree in sense of a pear with time. The reference numeral "5" designates "green degree", and the reference numeral "4" designates "semi-green degree", and the reference numeral "3" designates "semi-mature degree". The reference numeral "2" designates "mature degree", and the reference numeral "1" designates "over-mature degree". The green degree means the texture of flesh pear, and the mature degree means the texture of mature pear, so called buttery state.

As is apparent from FIGS. 5 and 6, the flesh hardness of the pear is decreased to 2.5 between the seventh day and the ninth day of the measurement. In this case, the kinetic property of the pear is changed drastically, and then, the texture of the pear turns into a buttery state. Thereafter, the mature degree of the pear proceeded, and turns into an over-mature degree at the fifteenth day of the measurement. However, the flesh hardness is not almost changed after the tenth day of the measurement from FIG. 5. Therefore, in the conventional technique, the flesh hardness is not correlated with the mature degree in sense.

The above result teaches that in the conventional technique, the food physicality can be detected on the kinetic property, but the subtle mature degree of the food can not be detected because the complicated and subtle physicality of food such as pear can not be detected on the kinetic properties of food such as hardness or adhesive force.

SUMMARY OF THE INVENTION

It is an object of the present invention to provide a device and a method for measuring and quantifying a mature degree of a food precisely.

In order to achieve the above object, in the present invention, a thrust jig with a concave-convex shape on the side is pierced into a food sample to generate and detect an oscillation spectrum or an acoustic spectrum. The measured spectrum includes various information of the food sample, so that the mature degree can be quantified if the spectrum is analyzed in main component.

The invention claimed in claim 1 relates to a device for measuring a food physicality, comprising:

a thrust jig with a concave-convex shape on a side thereof, a conveying means to convey the thrust jig to a food sample, a fastening means to fasten the thrust jig and the conveying means, an oscillation detecting means to detect an oscillation which is generated when the thrust jig is pierced into the food sample, an amplifying means to amplify an oscillation signal detected at the oscillation detecting means, a Fourier transformation means to Fourier-transform the oscillation signal from the amplifying means into an oscillation spectrum, a coefficient table storing predetermined coefficients, a calculating means to calculate the oscillation spectrum and the coefficient table to provide a given data to be employed as a texture of the food sample.

In this case, the texture of the food sample can be quantified precisely using the oscillation spectrum generated at the pierce of the thrust jig.

The conveying means may include a piston fastened to the thrust jig, a cylinder to which the piston is engaged, and a liquid pump to charge and discharge a liquid in or from the cylinder so as to press the piston down in the cylinder by the pressure of the liquid. In this case, since an unnecessary oscillation is removed, the oscillation spectrum can be obtained precisely.

In the Fourier transformation means, the oscillation spectrum may be divided by plural frequency segments within a predetermined frequency range. In this case, the calculating process can be simplified and thus, the calculating means can be simplified.

The coefficient table may be composed of eigenvectors obtained from a main component analysis for plural oscillation spectra of food samples with their respective different textures. In this case, the texture of the food sample can be obtained as a main component value on the eigenvectors.

The eigenvectors may be eigenvectors of a first main component through a N-th main component. In this case, the first main component value through the N-th main component value can be obtained.

The thrust jig is made of a columnar body with the concave-convex shape on the side thereof. In this case, the oscillation can be easily generated in the food sample.

The invention claimed in claim 7 relates to a method for measuring a food physicality, comprising the steps of:

piercing a thrust jig with a concave-convex shape on a side thereof into a food sample, detecting an oscillation signal generated between the thrust jig and the food sample, Fourier transforming the oscillation signal into an oscillation spectrum, dividing the oscillation spectrum by plural frequency segments within a given frequency range to obtain a data row relating to intensities of divided segments of the oscillation spectrum, performing a main component analysis for the data row to obtain a main component value of the oscillation spectrum as a texture of the food sample.

In this case, the main component analysis is performed on coefficient table relating to eigen values of said data row.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to the accompanying drawings.

Figure 1:
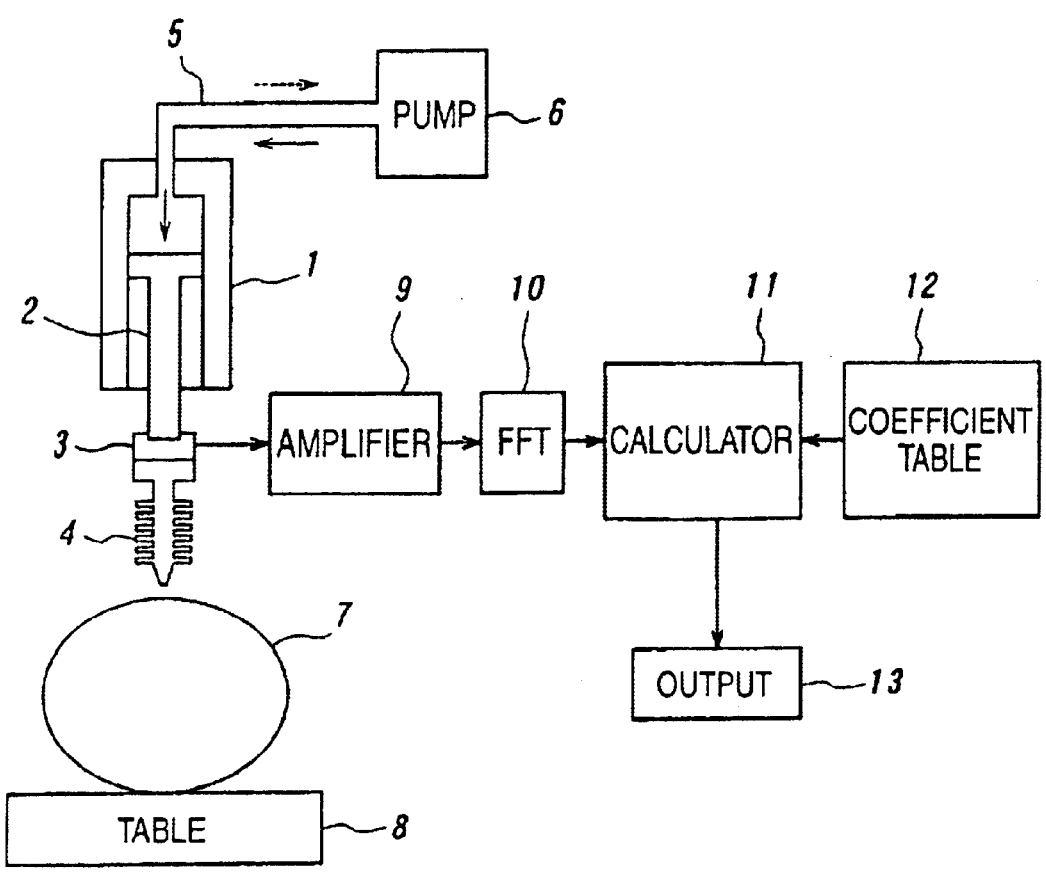
FIG. 1 is a schematic view showing a device for measuring a food physicality according to the present invention.

FIG. 1 is a schematic view showing a device for measuring a food physicality according to the present invention. In the device, a food sample 7 is set on a table 8, and a thrust jig 4 with a concave-convex shape on the side is disposed. A piezo element 3 as an oscillation detecting means is fastened to a piston 2 which is installed in a cylinder 1 which is connected to a liquid pump 6 via a tube 5. The piston 2 is moved vertically by charging or discharging a liquid in or from the cylinder 1 from the pump 6 on direction signal.

In the measurement, the liquid is charged into the cylinder 1 from the pump 6 along the solid line to press the piston 2 down and thus, pierce the thrust jig 4 into the food sample 7. The piercing rate of the thrust jig is determined appropriately by changing the charging rate of the liquid.

An oscillation at the piercing of the thrust jig 4 is detected with the piezo element 3, and then, amplified at an amplifying means 9. The thus obtained amplified oscillation signal is input into a Fourier transformation means 10 to be transformed on Fourier transformation. The thus obtained transformation signal is divided by plural frequency segments on a coefficient table 12, and introduced into a calculator 11, where the texture of the food sample is calculated on the divided transformation signal and the coefficient table.

Figure 2:
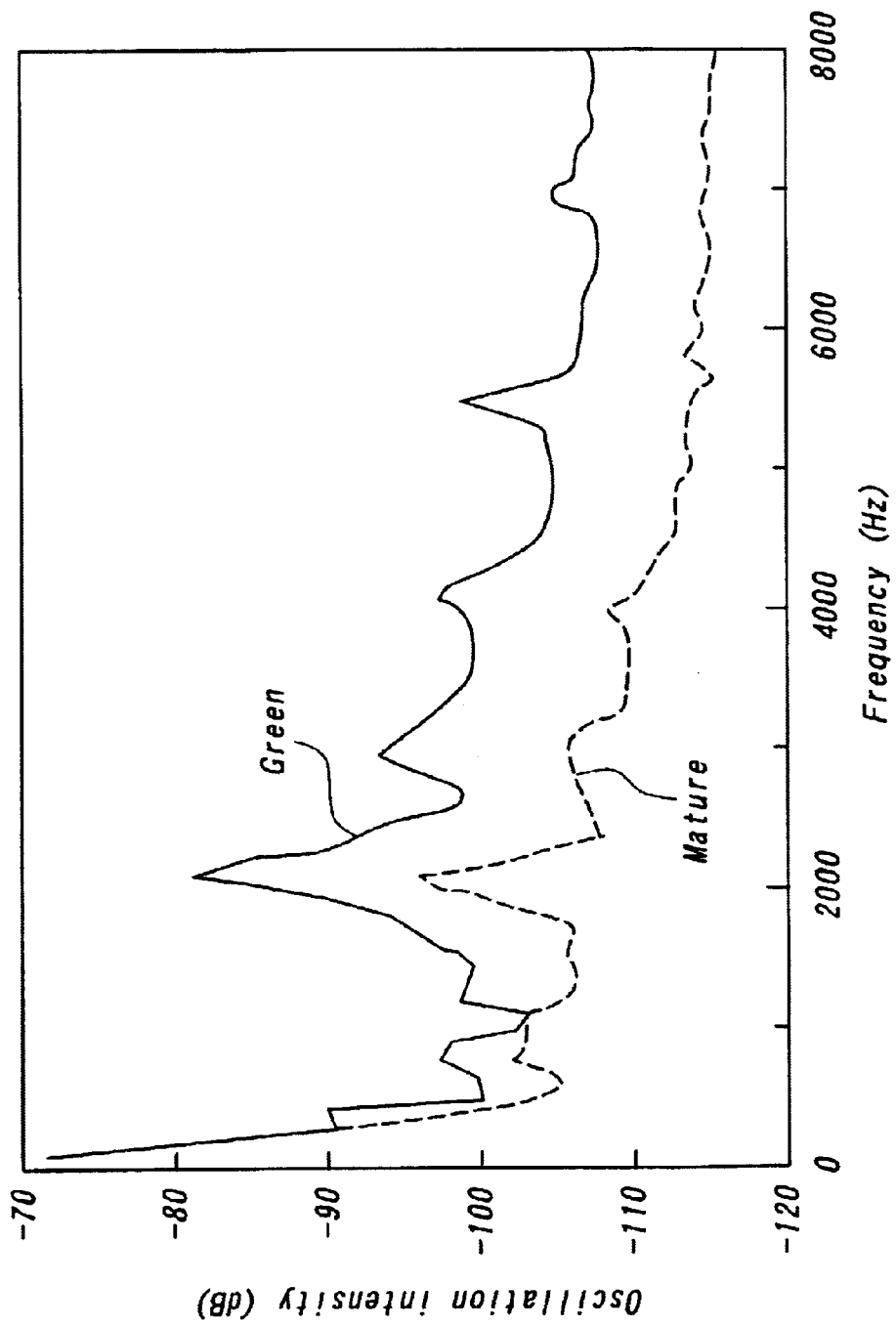
FIG. 2 is a graph showing oscillation spectra of pears with different mature degrees.

FIG. 2 is a graph showing the oscillation spectra of a green pear and a mature pear which are Fourier-transformed. The oscillation spectra of the green pear and the mature pear exhibit their different frequency dependence, particularly within a frequency range of 2000–8000 Hz. Herein, the analyzing method for the pear will be explained on the oscillation spectra of FIG. 2, but the analyzing method to be explained below can be applied for another food sample such as a food or a fruit.

The inventor found out a significant relation between the textures of pears with their different mature degrees and the main components of the oscillation spectra thereof on the main component analysis for the oscillation spectra of the pears. The main component analysis of the oscillation spectra and the setting method of the coefficient table will be explained hereinafter.

J pears with different mature degrees are prepared, and measured in oscillation spectrum. Each oscillation spectrum is divided by N frequency segments, and then, transformed into data rows $(X_{11}, X_{12}, \ldots X_{1N})$. If the above operation is carried out for the J pears, J date lows can be obtained. If the main component analysis is performed for the J data rows to make the correlative matrixes and the eigen values, their eigenvectors of the first main component through the p-th main component can be obtained. The relation between the data rows and the eigen values are listed in Table 1.

TABLE 1

| | | Variable i (i is integer number) | | | | |
|---|---|---|---|---|---|---|
| | | 1 | 2 | 3 | 4 | ... N |
| Data rows relating to tools with different mature degrees (j is integer number) | 1 | $X_{11}$ | $X_{12}$ | $X_{13}$ | $X_{14}$ | ... $X_{1N}$ |
| | 2 | $X_{21}$ | $X_{22}$ | $X_{23}$ | $X_{24}$ | ... $X_{2N}$ |
| | 3 | $X_{31}$ | $X_{32}$ | $X_{33}$ | $X_{34}$ | ... $X_{3N}$ |
| | ... | ... | ... | ... | ... | ... |
| | j | $X_{j1}$ | $X_{j2}$ | $X_{j3}$ | $X_{j4}$ | ... $X_{jN}$ |
| First main component eigenvector | | $a_{11}$ | $a_{12}$ | $a_{13}$ | $a_{14}$ | ... $a_{1N}$ |
| Second main component eigenvector | | $a_{21}$ | $a_{22}$ | $a_{23}$ | $a_{24}$ | ... $a_{2N}$ |
| ... | | ... | ... | ... | ... | ... |
| p-th main component eigenvector | | $a_{p1}$ | $a_{p2}$ | $a_{p3}$ | $a_{p4}$ | ... $a_{pN}$ |

If the eigenvectors, $a_{pi}$, for their respective main components are multiplied with the data rows, $(X_{1i}, X_{2i}, \ldots X_{ji})$ the first main component value through the p-th main component value can be obtained for each data row. Therefore, the eigen values are set as the coefficient table, the main components of the divided oscillation spectrum can be easily calculated on the data row.

Concrete embodiment will be shown in Table 2, where data rows of pears with different mature degree are listed. In this case, each oscillation spectrum is divided by 80 frequency segments per 100 Hz within a frequency range of 100–8000 Hz. In another embodiment, each oscillation spectrum can be divided by a different frequency segment number and a different frequency range.

TABLE 2

| | | \multicolumn{9}{c}{Frequency (Hz)} | | | | | | | | |
|---|---|---|---|---|---|---|---|---|---|---|---|
| | | 100 | 200 | 300 | 400 | ... | 7600 | 7700 | 7800 | 7900 | 8000 |
| Mature degree | 5.00 | −72.05 | −81.16 | −90.35 | −89.73 | ... | −106.9 | −107.3 | −107.3 | −107.4 | −106.4 |
| | 4.33 | −73.16 | −80.60 | −93.28 | −83.09 | ... | −109.0 | −108.3 | −109.0 | −107.8 | −106.5 |
| | 3.67 | −74.30 | −83.53 | −91.59 | −89.04 | ... | −109.9 | −109.5 | −109.8 | −109.5 | −108.6 |
| | 3.00 | −72.05 | −85.29 | −91.98 | −91.48 | ... | −108.8 | −108.7 | −109.2 | −109.2 | −109.5 |
| | 2.00 | −72.45 | −83.46 | −91.03 | −93.93 | ... | −115.7 | −114.0 | −115.3 | −115.6 | −115.0 |
| | 1.67 | −71.17 | −84.37 | −92.40 | −94.59 | ... | −115.3 | −114.9 | −115.5 | −115.6 | −115.7 |

From the data rows listed in Table 2 is made the correlation matrixes and the eigen values, to calculate the eigenvectors of the first main component. The calculated eigenvectors of the first main component are listed in Table 3. In this embodiment, the eigenvectors are employed as the coefficient Table. However, other eigenvectors of a different main component may be employed on the food physicality.

TABLE 3

| | \multicolumn{9}{c}{Frequency (Hz)} | | | | | | | | |
|---|---|---|---|---|---|---|---|---|---|
| | 100 | 200 | 300 | 400 | ... | 7600 | 7700 | 7800 | 7900 | 8000 |
| First main component eigenvector | −0.086 | −0.037 | 0.034 | 0.073 | ... | 0.120 | 0.120 | 0.120 | 0.119 | 0.118 |

Figure 3:
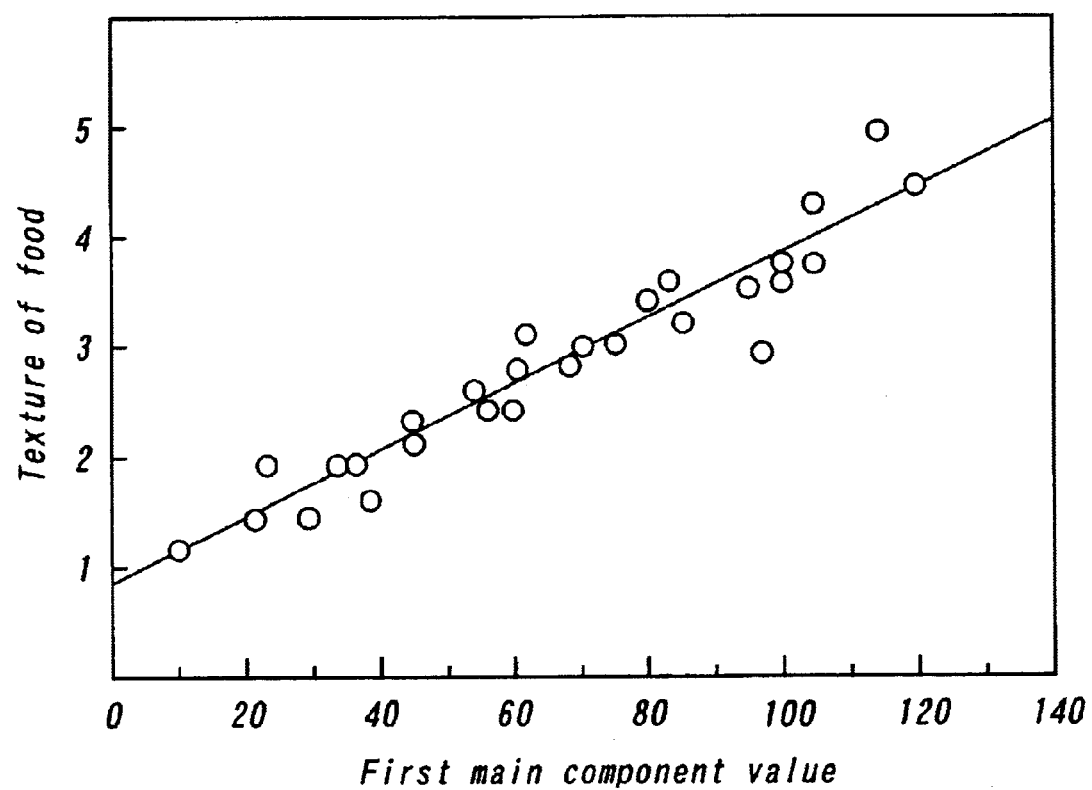
FIG. 3 is a graph showing the relation between the first main component of the oscillation spectrum and the mature degree of a pear.

FIG. 3 shows the relation between the first main components and the mature degree of the pears with the different mature degrees. The abscissa axis designates the first main component values of the pears, and the vertical axis designates the mature degree of the pears. The reference numeral "5" designates "green degree", and the reference numeral "4" designates "semi-green degree", and the reference numeral "3" designates "semi-mature degree". The reference numeral "2" designates "mature degree", and the reference numeral "1" designates "over-mature degree". As is apparent from FIG. 3, the first main component values are correlated with the mature degrees by a correlation coefficient of 0.93. Therefore, the mature degree of the pear can be quantified by the first main component value. In order to quantify the mature degree precisely, a high order main component value may be employed.

In another embodiment, as mentioned above, each oscillation spectrum can be divided by a different frequency segment number and a different frequency range on food physicality.

The thrust jig 4 is formed so as to generate a given oscillation in the food sample 7 in pierce. Concretely, the thrust jig 4 can be formed so as to have a shape illustrated in FIG. 4.

Figure 4A:
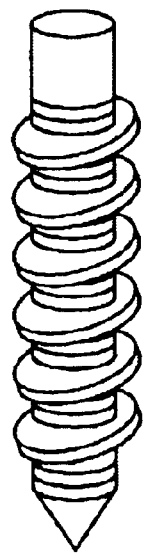
FIGS. 4a–4d are schematic views showing various embodiments for the thrust jig.

In FIG. 4a, the thrust jig 4 is formed so as to have circular helical flanges along the periphery of a cusped columnar body. Herein, the cusped body may be formed in elliptical columnar shape or rectangular columnar shape. The helical flange may have another shape such as rectangular shape or elliptical shape. Some or all of the flanges may have notches.

Figure 4B:
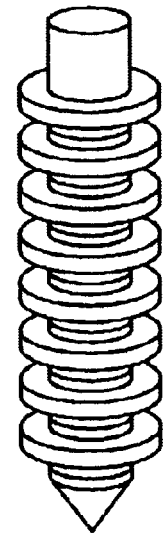

In FIG. 4b, the thrust jig 4 is formed so as to have circular flanges along the periphery of a cusped columnar body. The flanges may be attached horizontally or obliquely to the cusped body. The cusped body may be formed in elliptical columnar shape or rectangular columnar shape. The flange may have another shape such as rectangular shape or elliptical shape. Some or all of the flanges may have notches.

Figure 4C:
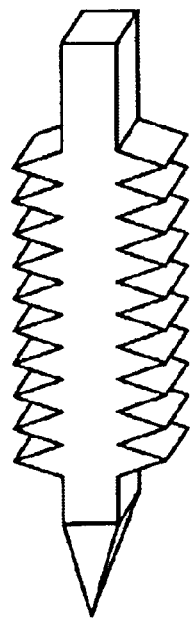

In FIG. 4c, the thrust jig 4 is made of a rectangular cusped body of which the sides are processed in sawedged shape. The cusped body may be formed in elliptical columnar shape or another rectangular columnar shape. Some notches may be formed at the cusped body.

Figure 4D:
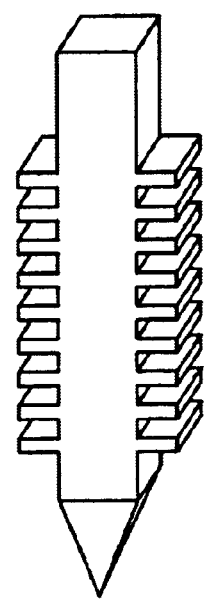
Figure 5:
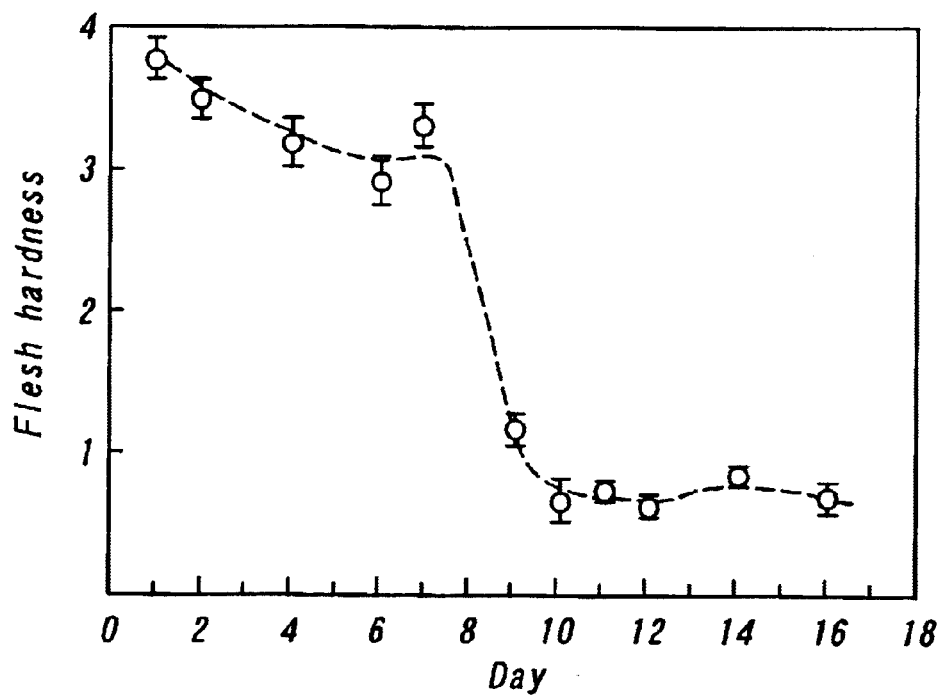
FIG. 5 is a graph showing the flesh hardness of a pear with time.
Figure 6:
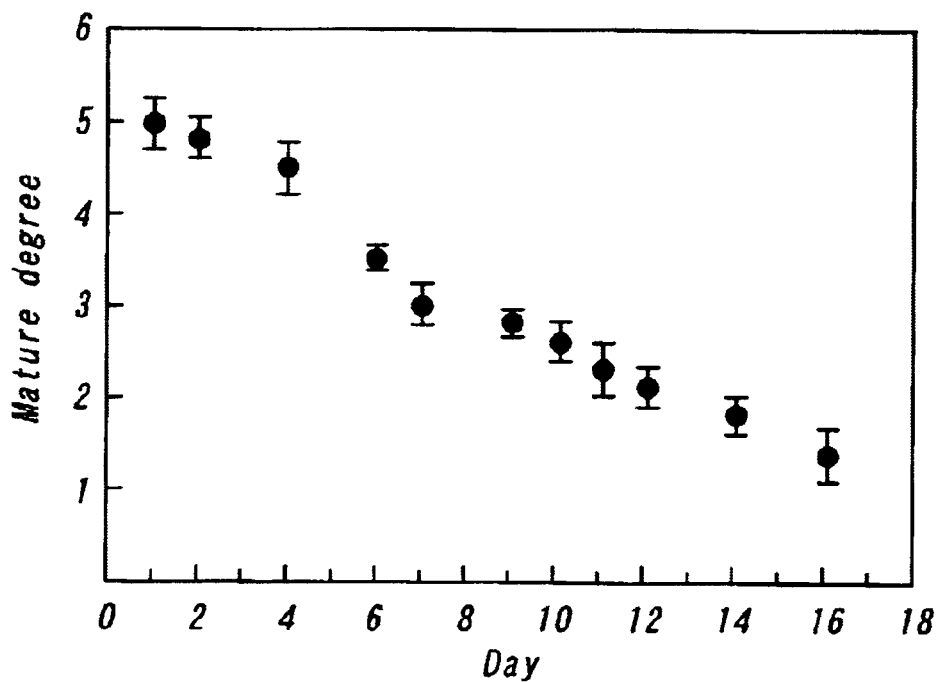
FIG. 6 is a graph showing the mature degree in sense of a pear with time.

In FIG. 4d, the thrust jig 4 is made of a rectangular cusped body of which the sides are processed in zigzag shape. The cusped body may be formed in elliptical columnar shape or another rectangular columnar shape. Some notches may be formed at the cusped body.

Although the present invention was described in detail with reference to the above examples, this invention is not limited to the above disclosure and every kind of variation and modification may be made without departing from the scope of the present invention.

In the present invention, as mentioned above, a thrust jig with a concave-convex shape on the side is pierced into a food sample to generate and detect an oscillation spectrum or an acoustic spectrum, which is divided by frequency segments and analyzed in main component. Therefore, the texture of a food can be quantified, which is difficult by a conventional technique.

What is claimed is:

1. A device for measuring a food physicality, comprising:
   a thrust jig with a concave-convex shape on a side thereof,
   a conveying means to convey said thrust jig to a food sample,
   a fastening means to fasten said thrust jig and said conveying means,
   an oscillation detecting means to detect an oscillation which is generated when said thrust jig is pierced into said food sample,
   an amplifying means to amplify an oscillation signal detected at said oscillation detecting means,
   a Fourier transformation means to Fourier-transform said oscillation signal from said amplifying means into an oscillation spectrum,
   a coefficient table storing predetermined coefficients,
   a calculating means to calculate said oscillation spectrum and said coefficient table to provide a given data to be employed as a texture of said food sample.

2. The measuring device as defined in claim 1, wherein said conveying means includes a piston fastened to said thrust jig, a cylinder to which said piston is engaged, and a liquid pump to charge and discharge a liquid in or from said cylinder so as to press said piston down in said cylinder by the pressure of said liquid.

3. The measuring device as defined in claim 1, wherein in said Fourier transformation means, said oscillation spectrum is divided by plural frequency segments within a predetermined frequency range.

4. The measuring device as defined claim 2, wherein in said Fourier transformation means, said oscillation spectrum is divided by plural frequency segments within a predetermined frequency range.

5. The measuring device as defined in claim 3, wherein said coefficient table is composed of eigenvectors obtained from a main component analysis for plural oscillation spectra of food samples with their respective different textures.

6. The measuring device as defined in claim 4, wherein said eigenvectors are eigenvectors of a first main component through a N-th main component.

7. The measuring device as defined in claim 4, wherein said eigenvectors are eigenvectors of a first main component through a N-th main component.

8. The measuring device as defined in claim 1, wherein said thrust jig is made of a columnar body with said concave-convex shape on said side.

9. The measuring device as defined in claim 2, wherein said thrust jig is made of a columnar body with said concave-convex shape on said side.

10. The measuring device as defined in claim 3, wherein said thrust jig is made of a columnar body with said concave-convex shape on said side.

11. The measuring device as defined in claim 4, wherein said thrust jig is made of a columnar body with said concave-convex shape on said side.

12. The measuring device as defined in claim 5, wherein said thrust jig is made of a columnar body with said concave-convex shape on said side.

13. The measuring device as defined in claim 6, wherein said thrust jig is made of a columnar body with said concave-convex shape on said side.

14. The measuring device as defined in claim 7, wherein said thrust jig is made of a columnar body with said concave-convex shape on said side.

15. A method for measuring a food physicality, comprising the steps of:

piercing a thrust jig with a concave-convex shape on a side thereof into a food sample, detecting an oscillation signal generated between said thrust jig and said food sample, Fourier-transforming said oscillation signal into an oscillation spectrum, dividing said oscillation spectrum by plural frequency segments within a given frequency range to obtain a data row relating to intensities of divided segments of said oscillation spectrum, performing a main component analysis for said data row to obtain a main component value of said oscillation spectrum as a texture of said food sample.

16. The measuring method as defined in claim 15, wherein said main component analysis is performed on coefficient table relating to eigen values of said data row.

* * * * *